(12) United States Patent
Lerman et al.

(10) Patent No.: US 6,844,440 B2
(45) Date of Patent: Jan. 18, 2005

(54) PROCESS FOR THE PREPARATION OF DONEPEZIL

(75) Inventors: Ori Lerman, Givatayim (IL); Joseph Kaspi, Givatayim (IL); Oded Arad, Rehovot (IL); Mohammed Alnabari, Hura (IL); Yana Sery, Beer Sheva (IL)

(73) Assignee: Chemagis Ltd., Tel Aviv (IL)

( * ) Notice: Subject to any disclaimer, the term of this patent is extended or adjusted under 35 U.S.C. 154(b) by 0 days.

(21) Appl. No.: 10/459,662

(22) Filed: Jun. 11, 2003

(65) Prior Publication Data
US 2004/0048893 A1 Mar. 11, 2004

(30) Foreign Application Priority Data
Jul. 30, 2002 (IL) .................................................. 150982

(51) Int. Cl.[7] .......................................... C07D 211/06
(52) U.S. Cl. .................. 546/206; 546/195; 546/233
(58) Field of Search ............................... 546/195, 206, 546/235

(56) References Cited

U.S. PATENT DOCUMENTS

| | | |
|---|---|---|
| 5,606,064 A | 2/1997 | Lensky |
| 6,252,081 B1 | 6/2001 | Iimura |

FOREIGN PATENT DOCUMENTS

| | | |
|---|---|---|
| EP | 296560 B1 | 2/1996 |
| EP | 711756 B1 | 7/1998 |
| WO | WO 97/22584 A1 | 6/1997 |
| WO | WO 99/36405 A1 | 7/1999 |

*Primary Examiner*—Cecilia J. Tsang
*Assistant Examiner*—Raymond Covington
(74) *Attorney, Agent, or Firm*—Leydig, Voit & Mayer, Ltd.

(57) ABSTRACT

The invention provides a process for the preparation of a compound of the formula 6 comprising the hydrolysis and decarboxylation of a compound of the formula 5 according to the reaction:

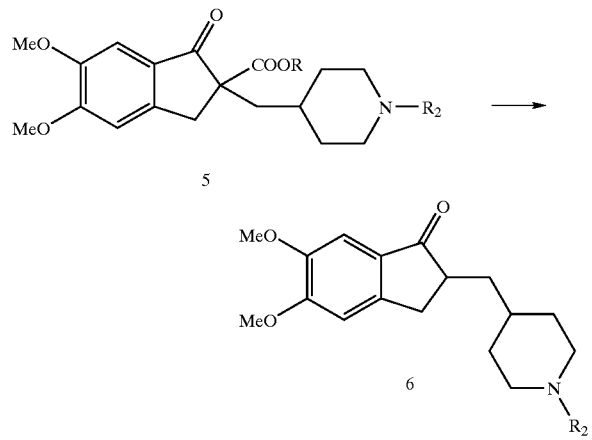

wherein R and $R_2$ independently a $C_1$–$C_4$ alkyl group or an aralkyl group.

45 Claims, No Drawings

PROCESS FOR THE PREPARATION OF DONEPEZIL

The present invention relates to a novel process for the preparation 1-benzyl-4-[(5,6-dimethoxyindan-1-on-2-yl) methyl]piperidine (Donepezil) and new intermediates thereof. Donepezil is used in the treatment of Alzheimer's disease.

PRIOR ART

Donepezil hydrochloride is a useful memory enhancer introduced by the Japanese pharmaceutical company Eisai. Its preparation was described in patent no. EP 296560. In this patent Donepezil was produced by reaction of 5,6-dimethoxy-1-indanone with 1-benzyl-4-formylpiperidine in the presence of a strong base, such as lithium diisopropylamide followed by reduction of the double bond. According to this method, Donepezil was obtained (Scheme 1).

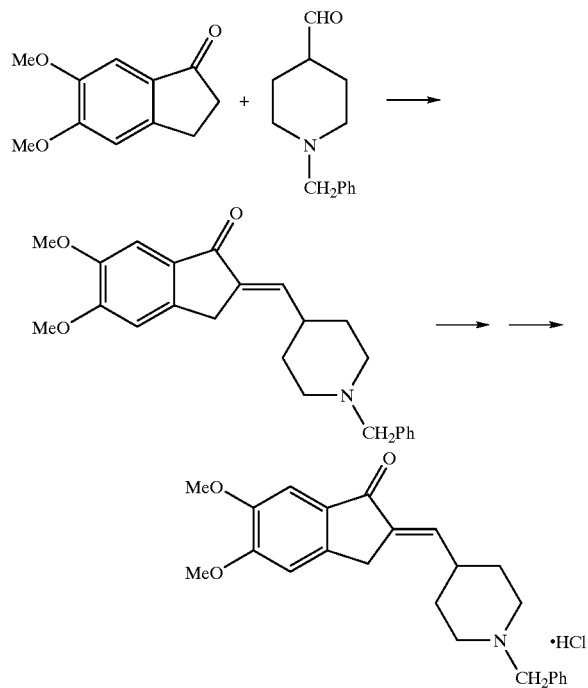

Patent application WO 99/36405 describes another process for the synthesis of Donepezil. According to this patent, 2-alkoxycarbonyl-1-indanones are reacted with (4-pyridinyl) methyl halide moiety followed by hydrolysis and decarboxylation to give the 2-(4-pyridinyl)methyl-1-indanone derivative. This is followed by reaction with benzyl halides to obtain the corresponding quaternary ammonium salt, and followed by hydrogenation of the pyridine ring to obtain Donepezil (Scheme 2).

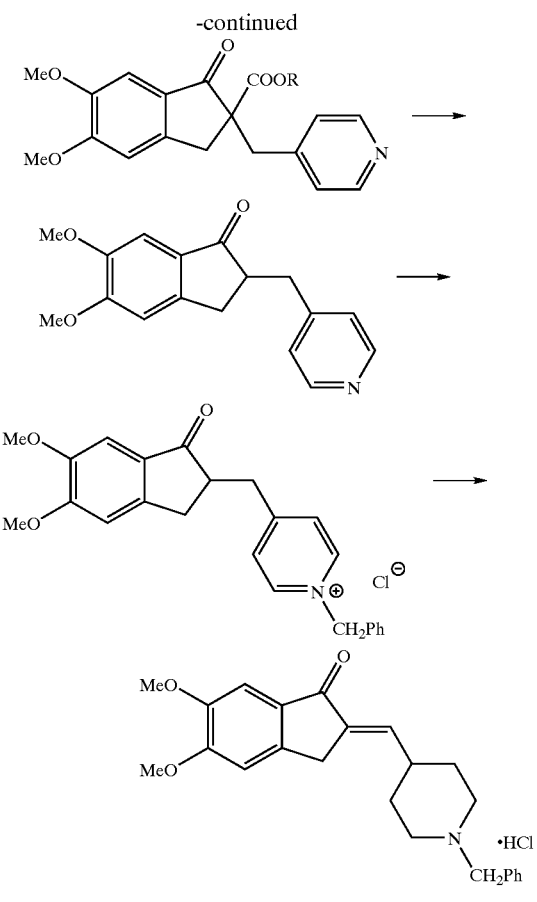

Patent application WO 97/22584 describes the preparation of Donepezil by reaction of pyridine-4-carboxyaldehyde with malonic acid to give 3-(pyridin-4-yl)-2-propenoic acid, followed by hydrogenation of the double bond to give 3-(piperidin-4-yl)-2-propionic acid. Reaction of this intermediate with methyl chloroformate afforded 3-[N-(methyloxycarbonyl) piperidin-4-yl]propionic acid. This was followed by reaction with oxalyl chloride to give methyl 4-(2-chlorocarbonylethyl)piperidin-1-carboxylate. Reaction with 1,2-dimethoxybenzene in the presence of aluminum chloride afforded methyl 4-[3-(3,4-dimethoxyphenyl)-3-oxopropyl]piperidin-1-carboxylate. Reaction with tetramethyldiaminomethane afforded 4-[2-(3, 4-dimethoxybenzoyl)allyl] piperidin-1-carboxylate. Reaction with sulfuric acid afforded methyl 4-(5,6-dimethoxy-1-oxoindan-2-yl)methylpiperidin-1-carboxylate. This was followed by treatment with base to give 5,6-dimethoxy-2-(piperidin-4-ylmethyl) indan-1-one, then reaction with benzyl bromide afforded Donepezil (Scheme 3).

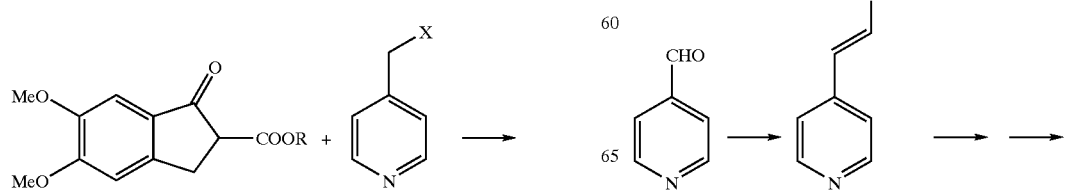

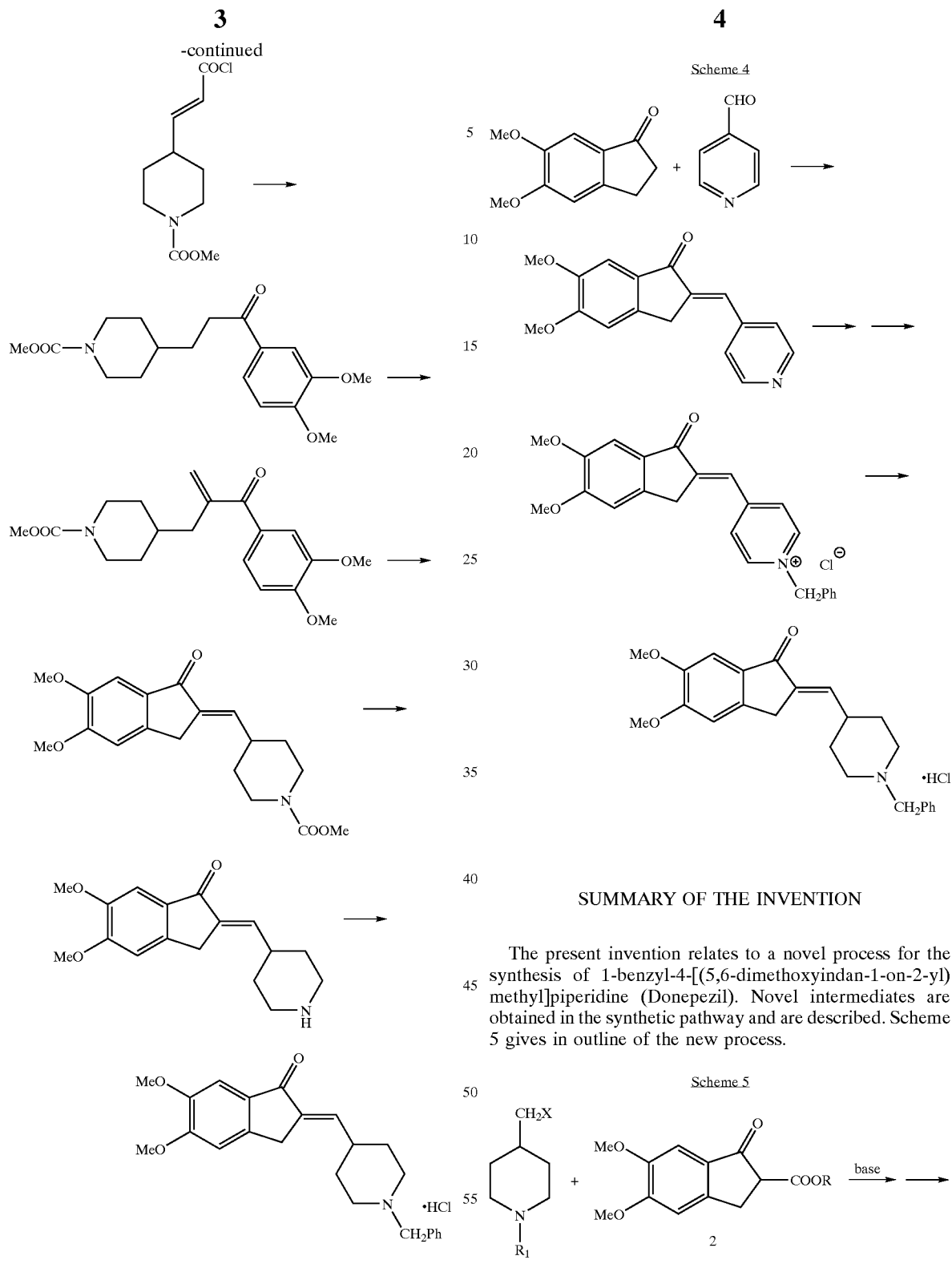

Patent application EP 711756 describes the preparation of Donepezil by reaction of 5,6-dimethoxy-1-indanone with pyridin-4-aldehyde to give 5,6-dimethoxy-2-(pyridin-4-yl) methylene indan-1-one. Reaction with benzyl bromide afforded 1-benzyl-4-(5,6-dimethoxyindan-1-on-2-ylidene) methylpyridinium bromide. Hydrogenation in the presence of platinum oxide afforded Donepezil (Scheme 4).

SUMMARY OF THE INVENTION

The present invention relates to a novel process for the synthesis of 1-benzyl-4-[(5,6-dimethoxyindan-1-on-2-yl) methyl]piperidine (Donepezil). Novel intermediates are obtained in the synthetic pathway and are described. Scheme 5 gives in outline of the new process.

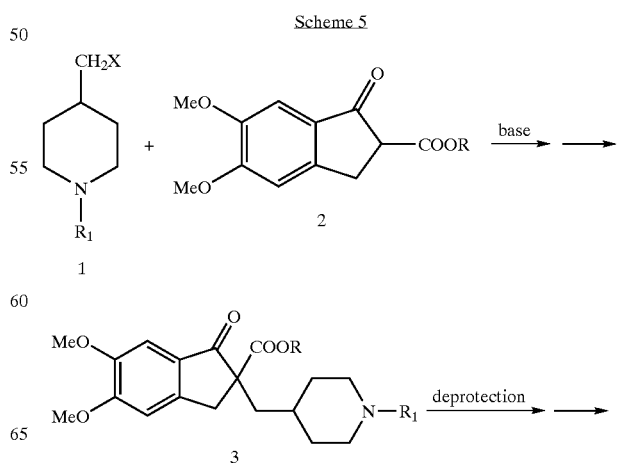

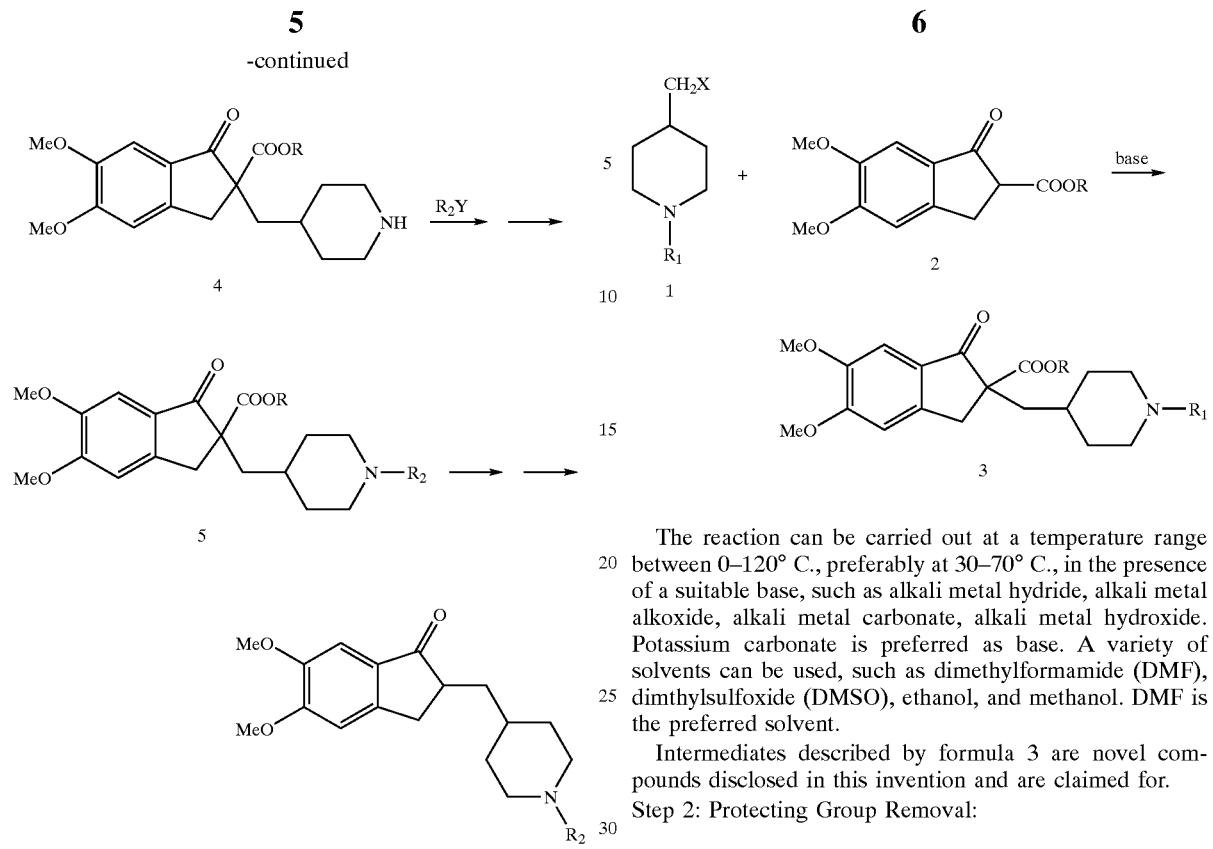

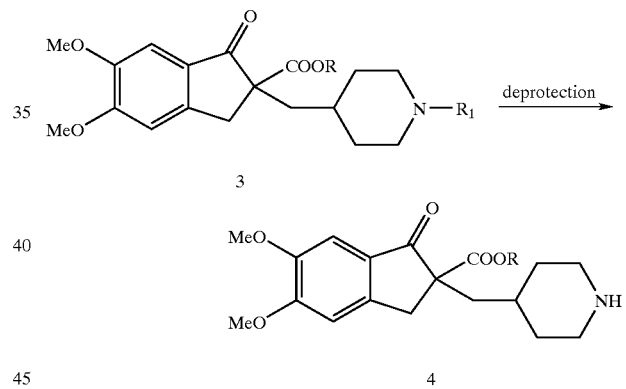

The reaction can be carried out at a temperature range between 0–120° C., preferably at 30–70° C., in the presence of a suitable base, such as alkali metal hydride, alkali metal alkoxide, alkali metal carbonate, alkali metal hydroxide. Potassium carbonate is preferred as base. A variety of solvents can be used, such as dimethylformamide (DMF), dimthylsulfoxide (DMSO), ethanol, and methanol. DMF is the preferred solvent.

Intermediates described by formula 3 are novel compounds disclosed in this invention and are claimed for.

Step 2: Protecting Group Removal:

N-protected activated-4-methylpiperidine (1) wherein X represents a leaving group and $R_1$ represents an N-protecting group reacts with 2-alkoxycarbonyl-5,6-dimethoxyindan-1-one (2) wherein R represents a $C_1$–$C_4$ alkyl group or an aralkyl group affording 4-[(2-alkoxycarbonyl-5,6-dimethoxy-indan-1-on-2-yl)methyl]-N-protected piperidine)] (3). Compound 3 is deprotected affording 4-[(2-alkoxycarbonyl-5,6-dimethoxy-indan-1-on-2-yl)methyl] piperidine having formula 4 wherein R is as defined above. This compound is reacted with a compound of the formula $R_2Y$ wherein $R_2$ is a $C_1$–$C_4$ alkyl group or an aralkyl group and Y is a leaving group to afford compound of type 5 wherein $R_2$ is and Y are as defined above. Compound 5 is subjected to hydrolysis followed by decarboxylation to afford compound of type 6 wherein $R_2$ is as defined above. In case where $R_2$ is a benzyl group compound 6 is Donepezil which is a useful drug for the treatment of Alzhiemer's disease.

Novel compounds represented by general formulae 3, 4 and 5 were isolated and identified as intermediates in the said process and are parts of this invention.

The invention is described in more details hereby:

Step 1: Coupling Reaction:

A compound of formula 1 is reacted with a compound of formula 2, wherein R is a $C_1$–$C_4$ alkyl group such as methyl, ethyl, t-Bu or an aralkyl group such as (optionally substituted) benzyl group. $R_1$ is any appropriate N-protecting group, such as t-Butoxycarbonyl (t-BOC), Benzyloxycarbonyl (CBZ), and triphenylmethyl. X is a leaving group, such as halide, mesylate or tosylate, preferably iodide.

The exact manner for removing the protecting group $R_1$ depends upon its nature. For example; removal of t-butoxycarbonyl (t-BOC) protecting group is carried out by trifluoroacetic acid (TFA) in an organic solvent like methylene chloride, toluene, chloroform or THF, preferably methylene chloride, while the removal of carbobenzoxycarbonyl (CBZ) protecting group can be done by hydrolysis using an acid, preferably 30% HBr in acetic acid at elevated temperature, in the presence of a solvent like methylene chloride, toluene, chloroform or THF, preferably toluene, or by catalytic hydrogenation using precious metal catalysis like palladium or platinum, preferably palladium on charcoal, in the presence of a C1–C4 alcohol as a solvent, preferably ethanol. Intermediates represented by general formula 4 {4-[(5,6-dimethoxy-2-alkoxycarbonylindan-1-on-2-yl)methyl] piperidine} are novel compounds disclosed in this invention.

Step 3: Substitution of the Nitrogen Atom

Compounds of type 5 wherein R is $C_1$–$C_4$ alkyl group and $R_2$ is $C_1$–$C_4$ alkyl group or an aralkyl group were obtained by reacting of compounds of general formula 4 with a compound of the formula $R_2Y$ wherein $R_2$ is as defined above and Y is a leaving group such as halide (chloride, bromide or iodide), mesylate or tosylate. The reaction can be carried out at temperature range of 0–100° C., preferably at 20–40° C., and in various solvents like THF, methylene chloride, chloroform, toluene, or a mixture thereof; methylene chloride is preferred solvent. The reaction is carried out in the presence of an organic or an inorganic base like an alkali metal hydroxide, an alkali metal carbonate or an organic amine, preferably triethylamine.

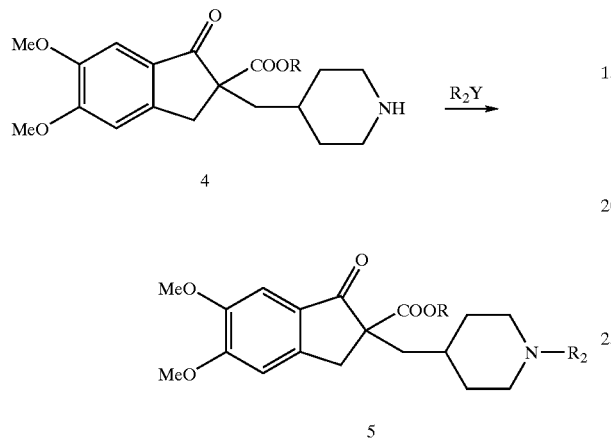

Intermediates of type 5 are novel compounds disclosed in this invention and are claimed for.

Step 4: Hydrolysis and Decarboxylation:

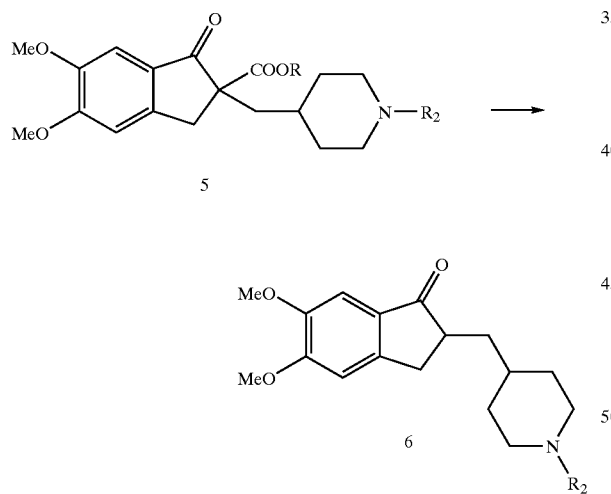

The method for the removal of the R group and decarboxylation depends on the nature of R. Reactions such as acidic or basic hydrolysis can be employed while basic hydrolysis is preferred. Bases like alkali metal hydroxides or carbonates may be employed, potassium carbonate is preferred. If R is a benzyl group catalytic hydrogenolysis can also be employed. Decarboxylation can be accomplished by heating using any appropriate solvent like ethanol, methanol, THF, DMF, DMSO or mixed solvents. Ethanol is the preferred solvent.

The preparation of Donepezil using the invention describes hereby consists of four easy chemical steps. No extreme conditions have to be used and starting materials are readily available. The yields are fair and the invention can be easily upscaled without any technical and safety problems.

Thus according to the present invention there is now provided process for the preparation of a compound of the formula 6 comprising the hydrolysis followed by decarboxylation of a compound of the formula 5 according to the reaction:

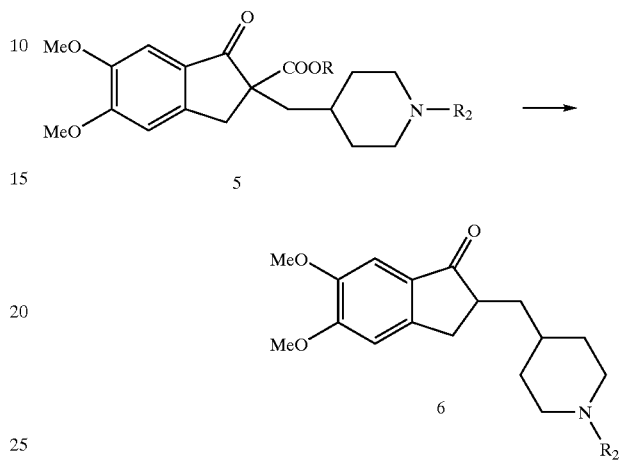

wherein R and $R_2$ are independently a $C_1$–$C_4$ alkyl group or an aralkyl group. In preferred embodiments of the present invention there is provided a process for the preparation of compound 6 as described above further characterized in that the preparation of compound 5 is achieved by the alkylation or aralkylation of compound 4 according to the reaction:

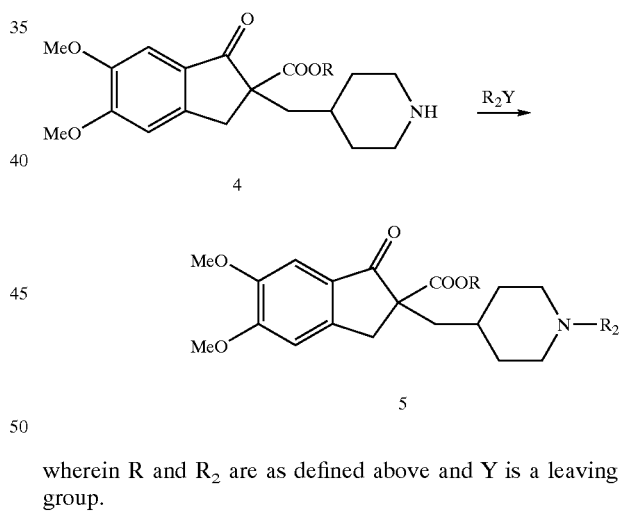

wherein R and $R_2$ are as defined above and Y is a leaving group.

In especially preferred embodiments of the present invention there is provided a process for the preparation of compound 6 as defined above further characterized that the preparation of compound 4 is achieved by the removal of the N-protecting group of compound 3 according to the reaction

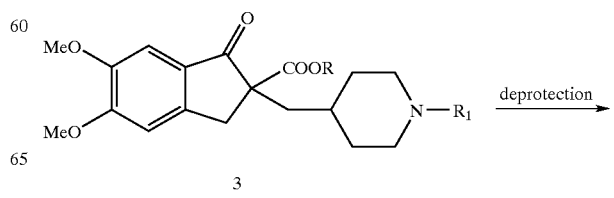

-continued wherein R is as defined above and $R_1$ is an N-protecting group.

In further especially preferred embodiments of the present invention there is provided a process for the preparation of compound 6 as defined above further characterized that the preparation of compound 3 is a achieved by the coupling of compounds 1 and 2 according to the reaction:

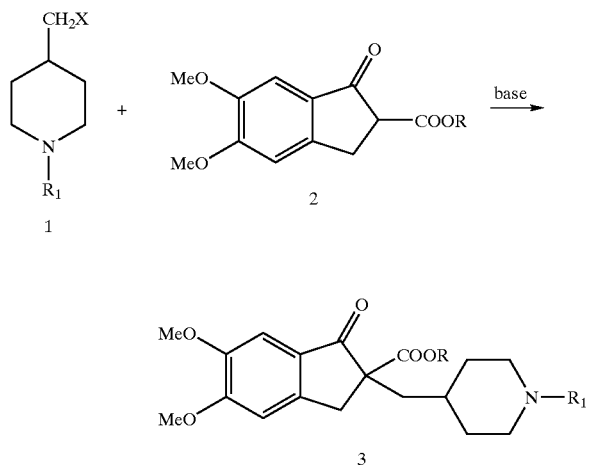

wherein R and $R_1$ are as defined above and X is a leaving group.

While the invention will now be described in connection with certain preferred embodiments in the following examples so aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples, which include preferred embodiments, will serve to illustrate the practice of this invention. It being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLES

Reference Example 1

2-ethoxycarbonyl-5,6-dimethoxyindan-1-one

This compound is prepared according to the procedure disclosed in EP 534859. To a suspension of sodium hydride (50% dispersion in oil, 20 g) in 240 mL of THF, diethyl carbonate was added and the mixture was stirred and refluxed for 90 min. A solution of 5,6-Dimethoxyindan-1-one (40 g) in THF (440 mL) was added, the mixture was heated under reflux for 3 h, then cooled and concentrated. Ethyl acetate (200 mL) was added, the organic layer was washed with water. The organic layer was dried over $MgSO_4$, filtered and the ethyl acetate was removed under reduced pressure. The title product was obtained in 98% yield.

Reference Example 2

N-CBZ-4-iodomethylpiperidine

This compound is prepared according to the procedure disclosed in U.S. Pat. No. 5,538,984.

Triphenylphosphine (31.2 gr) was added to a mixture of iodine (29.4 g) in toluene (1L). After 5 min, pyridine (18 ml) was added, followed by CBZ-piperidinemethanol (34.6 gr). The resulting mixture was heated and stirred at reflux for 1.5 h. The reaction mixture was allowed to cool to room temperature, and filtered. The filtrate was washed with saturated sodium metabisulfite and brine. The organic layer was dried over $MgSO_4$ and evaporated. The crude product was dissolved in ethyl acetate/hexane 1:5, and filtered through silica gel. The filtrate was evaporated under reduced pressure, and the crude product was crystallized from ethyl acetate/hexane.

Example 1

1-t-BOC-[4-((2-ethoxycarbonyl-5,6-dimethoxyindan-1-on)-2-yl)methyl] piperidine:

5,6-dimethoxy-2-ethoxycarbonylindan-1-one (7.68 g) was dissolved in DMF (340 mL). 1-t-BOC-piperidyl-4-methyliodide (12.3 g) and potassium carbonate (8.0 g) were added therein and the mixture was stirred at room temperature overnight. Ethyl acetate (200 mL) was added to the reaction mixture followed by water (200 mL) and the layers were separated. The organic layer was washed with water (3×50 mL) and then with saturated sodium chloride solution (200 mL). The organic layer was dried over $MgSO_4$, and the solvent was removed under reduced pressure. The title compound was isolated as a white-yellowish solid and recrystallized from ethyl acetate: hexane. 7.89 g (59% yield) of the title product was obtained and found to be pure by HPLC.

Mass spectrum m/e: 462[M+H$^+$]. Elemental analysis (calculated for $C_{25}H_{35}NO_7$): Calculated: C, 65.06%; H, 7.64%; N, 3.03%. Found: C, 64.92%; H, 7.32%; N, 3.31%. $^1$H-NMR(CDCl$_3$, δ(ppm)): 7.16(s, 1H), 6.90(s, 1H), 4.21(q, 2H), 3.98(s, 3H), 3.91(s, 3H), 3.67(2H), 2.63(m, 2H), 2.21 (m, 2H), 1.74(m, 2H), 1.59(m, 3H), 1.43(s, 9H), 1.26(t, 3H). $^{13}$C-NMR(CDCl$_3$, δ(ppm)): 200.6, 171.1, 156.0, 149.7, 148.4, 127.4, 107.1, 104.9, 79.3, 61.7, 60.8, 56.2, 44.0, 41.0, 36.7, 33.5, 28.4, 22.8, 14.0.

Example 2

1-t-BOC-[4-((5,6-dimethoxy-2-methoxycarbonylindan-1-on)-2yl)methyl]piperidine:

5,6-dimethoxy-2-methoxycarbonylindan-1-one (1.41 g) was dissolved in DMF (30 mL). Potassium carbonate (1.56 g) was added and the mixture was stirred for 30 min at room temperature. A solution of 1-t-BOC-piperidyl-4-methyliodide (2.2 g) dissolved in 10 mL DMF was added dropwise within 30 min. The mixture was heated gently to (45–50° C.) and the reaction mixture was stirred at 50° C. for 5 hrs. Ethyl acetate (30 mL) was added to the reaction mixture, and the solution was washed with water (3×30 mL). The organic layer was separated, dried over $MgSO_4$ and evaporated to give yellowish solid. The oil obtained was crystallized from ethyl acetate/n-hexane. 1.26 g of the title product (49.9% yield) were obtained as yellow crystals.

Mass spectrum m/e: 448[M+H$^+$]. $^1$H NMR(CDCl$_3$, δ(ppm)): 7.16(s, 1H), 6.89(s, 1H), 3.99(s, 3H), 3.90(s, 3H), 3.69(s, 3H).

Example 3

1-CBZ-[4-(5,6-dimethoxy-2-ethoxycarbonyl-1-indanon-2yl) methyl]piperidine:

5,6-dimethoxy-2-ethoxycarbonylindan-1-one (4.74 g) was dissolved in DMF (150 mL). Potassium carbonate (4.94 g) was added. 1-CBZ-piperidyl-4-methyliodide (9.09 g) dissolved in DMF (50 mL) was added dropwise and the mixture was stirred at room temperature overnight. Ethyl acetate (100 mL) was added and the mixture was washed with water (100 mL) and then with brine (50 mL). The organic layer was dried over MgSO$_4$, filtered and evaporated under reduced pressure. The crude product was crystallized from ethanol to give 4.94 g of the title product (59.1% yield).

Mass spectrum m/e: 496 [M+H$^+$]. Elemental analysis (calculated for C$_{28}$H$_{33}$NO$_7$): Calculated: C, 67.86%; H, 6.71%; N, 2.83%. Found: C, 67.64%; H, 6.68%; N, 3.07%. NMR (CDCl$_3$, δ(ppm)): 7.34(br s, 5H), 7.23(s, 1H), 6.89(s, 1H), 5.15(s, 2H), 4.21(q, 2H), 4.02(s, 3H), 3.94(s, 3H), 3.66(d, 1H), 3.03(d, 1H), 2.72(br t, 2H), 2.20(m, 2H), 1.57–1.73(m, 7H), 1.26(t, 3H).

Example 4

1-CBZ-[4-(5,6-dimethoxy-2-ethoxycarbonylindan-1-on-2-yl)methyl] piperidine:

To 5,6-dimethoxy-2-ethoxycarbonylindan-1-one (2.28 g) dissolved in DMF (80 mL), potassium carbonate (2.4 g) was added. Then, N-CBZ-piperidyl-4-methyltosylate (5.0 g) dissolved in DMF (25 mL) was added dropwise within 3 hrs. The mixture was stirred at ambient temperature 48 h, ethyl acetate (100 mL) was added therein and the mixture was rinsed with water (100 mL) and then with brine. The organic layer was dried over MgSO$_4$, filtered and evaporated under reduced pressure. The title product was obtained at 23% yield as confirmed by HPLC-MS analysis.

Example 5

1-CBZ-[4-(5,6-dimethoxy-2-ethoxycarbonyl-1-indanon-2-yl)methyl] piperidine:

To 5,6-dimethoxy-2-ethoxycarbonylindan-1-one (2.6 g) dissolved in DMF (50 mL), potassium carbonate (2.7 g) was added. N-CBZ-piperidyl-4-methylmesylate (4.6 g) dissolved in DMF (30 mL) was added dropwise within 3 hrs and the mixture was stirred for 48 h at ambient temperature. Ethyl acetate (100 mL) was added and the mixture was washed with water (100 mL) and then with brine (50 mL). The organic layer was dried over MgSO$_4$, filtered and evaporated under reduced pressure, HPLC of the crude indicate that the coupling product obtained at 5.6% yield and its identity was confirmed by HPLC-MS.

Example 6

4-[(5,6-Dimethoxy-2-ethoxycarbonylindan-1-on-2-yl) methyl]piperidine:

The product from example 1 (5.3 g) was dissolved in methylene chloride (50 mL), the solution was cooled to 0° C., trifluoroacetic acid (65.5 g) was added, and the solution was stirred at 0–5° C. for 30 minute. The methylene chloride and TFA were removed under reduced pressure, toluene (15 mL) was added and then removed under reduced pressure. A brownish oily product was obtained. The product was dissolved in a mixture of toluene and water (100 mL, 1:1), the mixture was stirred, the layers were allowed to separate and the organic layer was removed. The pH of the aqueous layer was brought to pH 8.0–8.5 with 1N-NaOH. The solution was extracted with ethyl acetate 3×50 mL, the organic layers were combined and washed with brine (20 mL), dried (MgSO$_4$) and filtered. The ethyl acetate was removed under reduced pressure. The crude product was crystallized from ethyl acetate/hexane to give 2.4 g of the title product (58% yield). The product was pure by HPLC.

Mass spectrum m/e: 362[M+H$^+$]. $^1$H-NMR(CDCl$_3$, δ(ppm)): 7.17(s, 1H), 7.08(s, 1H), 4.06(q, 2H), 3.89(s, 3H), 3.80(s, 3H), 3.21(m, 2H), 2.50(s, 2H), 2.01(m, 2H), 1.73(m, 3H), 1.30(m, 2H), 1.09(t, 3H).

Example 7

[4-(5,6-dimethoxy-2-ethoxycarbonylindan-1-on-2-yl) methyl]piperidine:

The product from example 2 (9.69 g) was dissolved in chloroform (100 mL), 30% HBr in acetic acid (23 mL) was added dropwise within 30 minute. The mixture was gently heated to 40° C. until full conversion was occurred (tested by HPLC). To the reaction mixture water (200 mL) was added and the mixture was stirred for 15 min. The aqueous solution was separated and washed with chloroform (100 mL). Sodium hydroxide solution (20%) was added until pH 10 was reached. The product was extracted with ethyl acetate (50 mL×4), the combined organic layer were dried over MgSO$_4$ and evaporated to obtained 4.9 g of the title compound (68.6% yield) the product was found to be pure by HPLC.

Example 8

1-Benzyl-4-[((5,6-dimethoxy-2-ethoxycarbonylindan-1-on)-2-yl)methyl]piperidine:

The product from example 8 (8.23 g) was dissolved in toluene (100 mL), triethylamine (15 mL) and benzyl chloride (2.9 mL) were added therein and the reaction mixture was heated to 35° C. and stirred overnight. The organic layer was washed with water and brine; then dried over MgSO$_4$ and evaporated. The crude product was crystallized from ethyl acetate-hexane to give 9.53 g of white solid, (89% yield).

Mass spectrum m/e: 452[M+H$^+$]. $^1$H NMR (CDCl$_3$, δ(ppm)): 7.29(m, 5H), 7.22(s, 1H), 6.88(s, 1H), 4.14(q, 2H), 3.97(s, 3H), 3.89(s, 3H), 3.70(m, 2H), 3.44(s, 2H), 3.01(d, 2H), 2.97(m, 2H), 2.0(m, 2H), 1.37(m, 2H), 1.23(m, 3H), 1.20(t, 3H). $^{13}$C NMR(CDCl$_3$, δ(ppm)): 200, 171, 149, 148, 138, 129–126, 107, 105, 63, 61.3, 58, 56, 53, 41, 36, 33, 18, 14. IR(NaCl, Nujol) ν(cm$^{-1}$): 2923, 2853, 1701(C=O), 1591, 1499, 1459, 1376. UV (MeOH) λ$_{max}$(nm): 207, 232, 272, 318.

Example 9

1-Methyl-4-((5,6-dimethoxy-2-ethoxycarbonyl-1-indanone)-2-yl)methylpiperidine:

Following the procedure described in example 8, the product obtained in example 2 (1.7 g), triethylamine (4 mL), CH$_2$Cl$_2$ (10 mL), and methyl iodide (0.67 g) in CH$_2$Cl$_2$ (10 mL) were reacted. After crystallization, 1.41 g of the title compound was obtained as white crystals in 80% yield.

Mass spectrum m/e: 376[M+H$^+$].

Example 10

1-Benzyl-[4-((5,6-dimethoxyindan-1-one)-2-yl)methyl] piperidine (Donepezil):

The product from example 8 (3.55 g,) was dissolved in ethanol-water mixture (5:1). Potassium hydroxide (2.05 g) was added and the solution was refluxed for 60 min. Water (50 ml) was added. And a yellowish precipitation was formed. Ethyl acetate was added, and the solvent was removed under reduced pressure. Donepezil free base was obtained as white solid. The product was crystallized from ethanol to obtain 2.3 g of the product (80% yield).

Mass spectrum m/e: 380[M+H$^+$]. $^1$H-NMR(CDCl$_3$, δ(ppm)): 7.63(brs, 2H), 7.44(brs, 3H), 7.11(s, 1H), 6.85(s, 1H), 4.16(s, 2H), 3.95(s, 3H), 3.89(s, 3H), 3.40(m, 2H), 3.25(m, 1H), 2.66(m, 4H), 2.06–1.96(m, 6H), 1.51(m, 1H).

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

All references, including publications, patent applications, and patents, cited herein are hereby incorporated by reference to the same extent as if each reference were individually and specifically indicated to be incorporated by reference and were set forth in its entirety herein.

What is claimed is:

1. A process for the preparation of a compound of the formula 6 comprising hydrolyzing and decarboxylating a compound of the formula 5 according to the reaction:

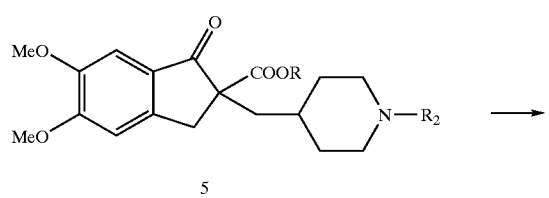

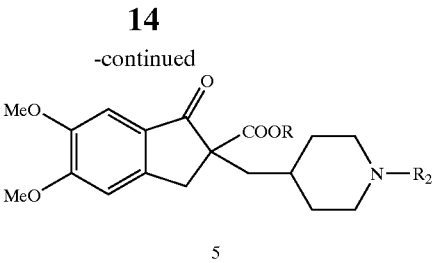

wherein R and R$_2$ are independently a C$_1$–C$_4$ alkyl group or an aralkyl group.

2. A process for the preparation of compound 6 as described in claim 1, further comprising preparing compound 5 by the alkylation or aralkylation of compound 4 according to the reaction:

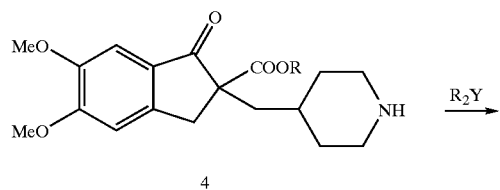

wherein R and R$_2$ are as defined in claim 1 and Y is a leaving group.

3. A process for the preparation of compound 6 according to claim 2, further comprising preparing compound 4 by the removal of the N-protecting group of compound 3 according to the reaction:

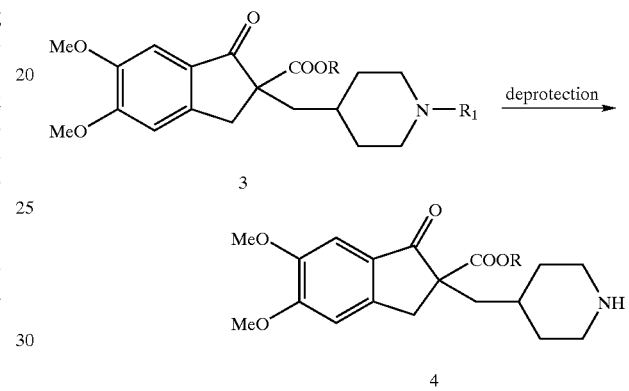

wherein R is as defined in claim 2, and R$_1$ is N-protecting group.

4. A process for the preparation of compound 6 according to claim 3, further comprising preparing compound 3 by the coupling of compounds 1 and 2 according to the reaction:

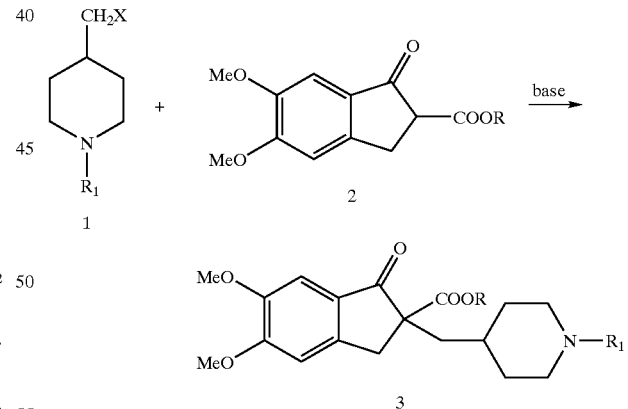

wherein R and R$_1$ are as defined in claim 3, and X is a leaving group.

5. A process according to claim 1 wherein the hydrolysis and decarboxylation are carried out in a solution, at elevated temperature and in the presence of a base.

6. A process according to claim 5 wherein the temperature is in the range of 60–100° C.

7. A process according to claim 5 wherein the base is a hydroxide or a carbonate of an alkali metal.

8. A process according to claim 7 wherein the base is potassium hydroxide.

9. A process according to claim 5 wherein the reaction is carried out in a mixture of a $C_1$–$C_6$ alcohol and water.

10. A process according to claim 9 wherein the reaction is carried out in the presence of ethanol and water.

11. A process according to claim 2 wherein the alkylation or aralkylation reaction is carried out in a solution, in the presence of an organic or an inorganic base.

12. A process according to claim 11 wherein the solvent is toluene, methylene chloride, chloroform, tetrahydrofuran (THF).

13. A process according to claim 11 wherein the solvent is methylene chloride.

14. A process according to claim 11 wherein the base is an alkali metal hydroxide, an alkali metal carbonate or an amine.

15. A process according to claim 11 wherein the base is triethylamine.

16. A process according to claim 3 wherein $R_1$ is benzyloxycarbonyl (CBZ).

17. A process according to claim 16 wherein the deprotection reaction is carried out in the presence of solvent, at elevated temperature using acid as catalyst.

18. A process according to claim 17 wherein the solvent is methylene chloride, toluene, chloroform or THF.

19. A process according to claim 18 wherein the solvent is toluene.

20. A process according to claim 17 wherein the acid is 30% solution of HBr in acetic acid.

21. A process according to claim 16 wherein the deprotection reaction is carried out in a solvent by hydrogenolysis in the presence of a precious metal catalyst.

22. A process according to claim 21 wherein the solvent is a $C_1$–$C_6$ alcohol.

23. A process according to claim 22 wherein the solvent is ethanol.

24. A process according to claim 21 wherein the catalyst is a supported palladium or platinum catalyst.

25. A process according to claim 24 wherein the catalyst is palladium on charcoal.

26. A process according to claim 3 wherein $R_1$ is t-butoxycarbonyl (t-BOC).

27. A process according to claim 26 wherein the deprotection is carried out in solution in a the presence of an acid.

28. A process according to claim 27 wherein the solvent is selected from the group consisting of methylene chloride, toluene, chloroform and THF.

29. A process according to claim 28 wherein the solvent is methylene chloride.

30. A process according to claim 28 wherein the acid is trifluoroacetic acid.

31. A process according to claim 4 wherein the coupling reaction is carried out in a solution, at elevated temperature and in the presence of a base.

32. A process according to claim 31 wherein the solvent is selected from the group consisting of dimethylformamide (DMF), dimethylsulfoxide (DMSO), ethanol and methanol.

33. A process according to claim 32 wherein the solvent is dimethylformamide.

34. A process according to claim 31 wherein the base is an alkali metal carbonate, alkali metal hydroxide, alkali metal hydride or alkali metal alkoxide.

35. A process according to claim 34 wherein the base is potassium carbonate.

36. A process according to claim 31 wherein the reaction is carried out within a temperature range of 30–70° C.

37. A process for the preparation of Donepezil comprising:
 a. coupling a compound of general formula 1 with a compound of general formula 2 wherein R is a $C_1$–$C_4$ alkyl group or an aralkyl group, $R_1$ is an N-protecting group, and X is a leaving group;
 b. deprotecting a compound of general formula 3, wherein R is a $C_1$–$C_4$ alkyl group or an aralkyl group, and $R_1$ is an N-protecting group;
 c. benzylating a compound of general formula 4 with a compound of formula $PhCH_2Y$, wherein Y is a leaving group; and
 d. hydrolyzing and decarboxylating a compound of general formula 5, wherein R is a $C_1$–$C_4$ alkyl group or an aralkyl group, and $R_2$ is benzyl.

38. A process according to claim 37 wherein step c is carried out with a benzylhalide.

39. Donepezil or salts thereof produced according to claim 37.

40. Compounds of general formula 3 wherein R and $R_1$ are as defined in claim 4.

41. Compounds as claimed in claim 40 wherein R is methyl or ethyl group and $R_1$ is CBZ or t-BOC group.

42. Compounds of general formula 4 or salts thereof wherein R is as defined in claim 3.

43. Compounds as claimed in claim 42 wherein R is methyl or ethyl group.

44. Compounds of general formula 5 or salts thereof wherein R and $R_2$ are as defined in claim 2.

45. Compounds as claimed in claim 44 wherein $R_2$ is benzyl group and R is ethyl or methyl group.

* * * * *